US006368481B1

(12) United States Patent
Sowa et al.

(10) Patent No.: US 6,368,481 B1
(45) Date of Patent: Apr. 9, 2002

(54) CASSETTE FOR ELECTROPHORESIS SYSTEM

(75) Inventors: Stefan Sowa, Uppsala; Jan-Olof Johansson, Knivsta; Anders Larsson, Bromma, all of (SE)

(73) Assignee: Amersham Pharmacia Biotech AB, Uppsala (SE)

(*) Notice: Subject to any disclaimer, the term of this patent is extended or adjusted under 35 U.S.C. 154(b) by 0 days.

(21) Appl. No.: 09/319,150
(22) PCT Filed: Sep. 29, 1998
(86) PCT No.: PCT/SE98/01766
  § 371 Date: Aug. 23, 1999
  § 102(e) Date: Aug. 23, 1999
(87) PCT Pub. No.: WO99/17109
  PCT Pub. Date: Apr. 8, 1999

(30) Foreign Application Priority Data

Oct. 1, 1997 (SE) .............................. 9703578

(51) Int. Cl.⁷ ....................... G01N 27/26; G01N 27/447
(52) U.S. Cl. ....................... 204/616; 204/456; 204/466; 204/606
(58) Field of Search ................. 204/616, 606, 204/456, 466

(56) References Cited

U.S. PATENT DOCUMENTS

| 4,975,173 A | 12/1990 | Tansamrit et al. .......... 204/620 |
| 5,582,702 A | 12/1996 | Cabilly et al. .............. 204/456 |
| 6,165,337 A | * 12/2000 | Stio .......................... 204/456 |

FOREIGN PATENT DOCUMENTS

| EP | 0155977 | 10/1985 |
| WO | 8704948 | 8/1987 |

* cited by examiner

*Primary Examiner*—Jill Warden
*Assistant Examiner*—John S. Starsiak, Jr.
(74) *Attorney, Agent, or Firm*—Birch, Stewart, Kolasch & Birch, LLP

(57) ABSTRACT

The invention concerns a cassette for an electrophoresis system including an essentially plate shaped body, which includes a first wall for supporting a gel plate, and a second wall for supporting buffer strips, the walls being connected to each other. Further, the second wall is displaceable with respect to the first wall between a first inactive position where the buffer strips are chemically and electrically separated from the gel plate and a second, active position where the buffer strips are in electrical and chemical contact with the gel plate.

10 Claims, 3 Drawing Sheets

CASSETTE FOR ELECTROPHORESIS SYSTEM

This application is the national phase under 35 U.S.C. §371 of PCT International Application No. PCT/SE98/01766 which has an International filing date of Sep. 29, 1998 which designated the United States of America.

BACKGROUND OF THE INVENTION

1. Field of the Invention

This invention concerns a cassette for an electrophoresis system including an essentially plate shaped body comprising wall means for supporting a gel plate.

This invention also concerns an electrophoresis system using such a cassette.

2. Description of the Background Art

Electrophoresis is a commonly used method for analysis, wherein charged molecules and particles migrate in a separation medium, usually a gel, which is subjected to an electrical field between two electrodes. Provided the electrical field is constant each molecule migrates with a constant speed which is determined by parameters such as field intensity and gel density but also by molecule parameters such as charge and size.

The separation medium is usually placed on a support and each side of the medium is contacted with an electrode buffer. The electrodes may be inserted in vessels containing the electrode buffers. The buffer solutions form both the electrolytic medium and a reservoir for ions to keep the pH and other parameters constant. After separation the molecules are detected and identified in different manners such as staining the gel or by optical means such as scanning by laser.

Gel electrophoresis is today routinely used for separating biomolecules such as proteins, peptides, nucleic acids etc. Often a lot of samples are handled e.g. in different types of screening or in clinical tests with samples from many patients. The electrophoretic conditions for different types of molecules are different and have to be adapted in each case. Thus, both the gel and the buffer solutions must be chosen for each type of sample.

The preparation of the electrophoresis process includes several rather laborious steps. A suitable gel is chosen and placed on a support. The gel is contacted with the buffer solutions. A common way is to have a gel slab in a cassette of glass or plastic in contact with the buffer solutions in buffer tanks. For each run the gel has to be placed on the support or the cassette be prepared. Then the buffer tanks are filled with buffer solutions and the samples are applied to the gel. To do away with the handling of buffer solutions in buffer tanks it has been suggested, in WO 87/04948, to incorporate the buffer substance in a gel material whereby the buffer is obtained in the form of a buffer strip. The buffer strips are much easier to handle, but still there remainder steps of adding all components together, which are time consuming and prevent automated handling. There is also a risk of mixing up samples with the many manual steps.

SUMMARY OF THE INVENTION

It is an aim of this invention to provide a solution to the above indicated problems and to provide a safe and effective means for use in an electrophoresis system.

This aim is obtained by providing a cassette and an electrophoresis system claimed in the claims. According to the invention a cassette for an electrophoresis system including an essentially plate shaped body is obtained. The plate shaped body comprises first wall means for supporting a gel plate and second wall means for supporting buffer strips, said wall means being connected to each other.

The cassette is characterized in that the second wall means are displaceable with respect to the first wall means between a first inactive position wherein the buffer strips are chemically and electrically separated from the gel plate and a second, active position where they are in electrical and chemical contact therewith.

With the cassette according to the invention it is possible to offer a "tailor-made", tuned unit comprising buffer, gel and added samples, a unit which can be added directly to the electrophoresis system. For each cassette, buffer strips and a gel plate which are specifically adapted for a particular application may be provided.

The buffer solution included in the buffer strips may readily be carefully adapted to the electrophoresis procedure to be performed, and by having the buffer strips chemically and electrically isolated from the gel plate, it is assured that no chemical influences, such as dilution or migration of buffer solution, affect the gel plate because of contact with the gel plate. By having the buffer strips isolated from the gel plate in the inactive position and not allowing electrical and chemical contact therebetween until after displacing the second wall means and thereby the buffer strips into the second, active, position it is therefore assured that the properties of the buffer strips are not changed or deteriorated, which could otherwise be the case.

In this manner the user of the cassette knows that the rust from the electrophoresis will have a certain quality. This is especially important in analysis where a high degree of accuracy is necessary. For example, in searching for a suitable donor for transplantation, HLA (human leukocyte antigen) analysis is made, as these antigens are known to be the major target molecules for transplantation rejection. On the nucleic acid level, it is then important that the DNA sequence in a specific position is very clear. The resolution of the sequence in a DNA analysis is determined byte buffers and the gel parameters and running conditions.

Further, an important advantage with a further aspect of the invention is that the samples may be loaded on the gel in the cassette, which in that case may be sealed or covered and the unit can then be stored. Traditionally, the samples are applied to the gel in the electrophoresis apparatus. With this invention it is easier to handle samples in a safe manner. Samplers like blood for exhale, have to be handled in special rooms due to, among other things, the risk of infection. The samples is prepared e.g. by centrifuging etc. and in the end is applied on the gel. With this invention all sample preparation can be made at one place and the cassette with samples can be stored for later use without any risk for mixing-up, contamination or transmission of infection.

U.S. Pat. No. 5,582,702 concerns a cassette wherein the gel body is in permanent contact with the buffer bodies. Therefore, this cassette suffers from the above-mentioned disadvantages.

By the second wall means being displaceable by means of a linear movement it is possible to predetermine the contact pressure by dimensioning the cassette itself.

By the second wall means being displaceable by means of a pivoting movement simplicity is obtained in manufacture as well as in handling. The contact between the buffer strips and the gel plate is easily obtained.

By the buffer strips being separated from the gel plate by means of removable isolating elements in the inactive position it is possible to manufacturing particularly compact cassettes.

By the buffer strips and at least a part of the gel plate being protected by protective strips in the inactive position separation against the environment is assured.

BRIEF DESCRIPTION OF THE DRAWINGS

The invention will now be described in greater detail with reverence to the drawings, wherein.

DETAILED DESCRIPTION OF THE PREFERRED EMBODIMENTS

Like elements are provided withheld same reference numbers.

Figure 1:
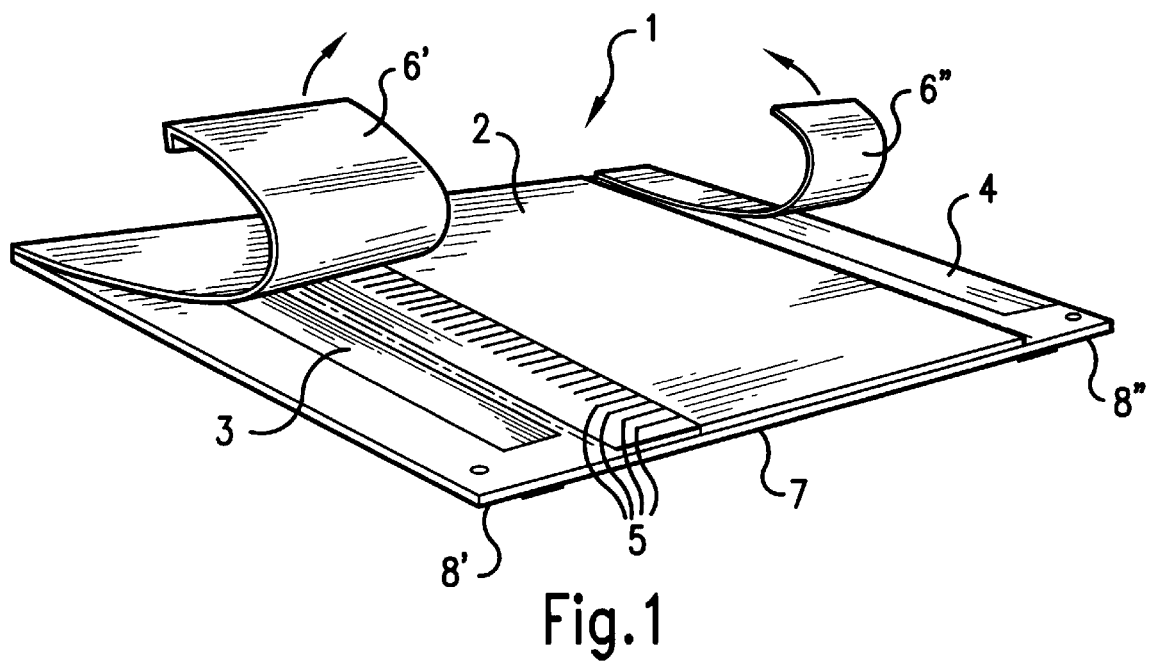
FIG. 1 is a perspective view of a cassette unit according to the invention.

In FIG. 1 the cassette unit which can be defined as a gel plate assembly includes a gel plate 2, which is supported by first wall means 7, in the shown embodiment manufactured from a synthetic material. On each side of the gel plate the cassette unit comprises buffer strips, namely a first buffer strip 3 and a second buffer strip 4. At the portion of the gel plate 2 which is closest to the first buffer strip 3, said gel plate is provided with sample wells 5 for receiving samples to be analyzed.

On each side of the first wall means 7 there are connected second wall means 8' and 8" which provide support for the first buffer strip 3 and the second buffer strip 4 respectively.

In FIG. 1 the cassette unit is in the inactive position, which means that there is no chemical or electrical contact between the respective buffer strip and the gel plate. These parts are thus separated 6' and 6" in the Figure indicate protective strips of an inert, preferably plastic material, which in the Figure is in the process of being removed from the parts of the cassette unit which they are covering in the inactive position.

Figure 2:
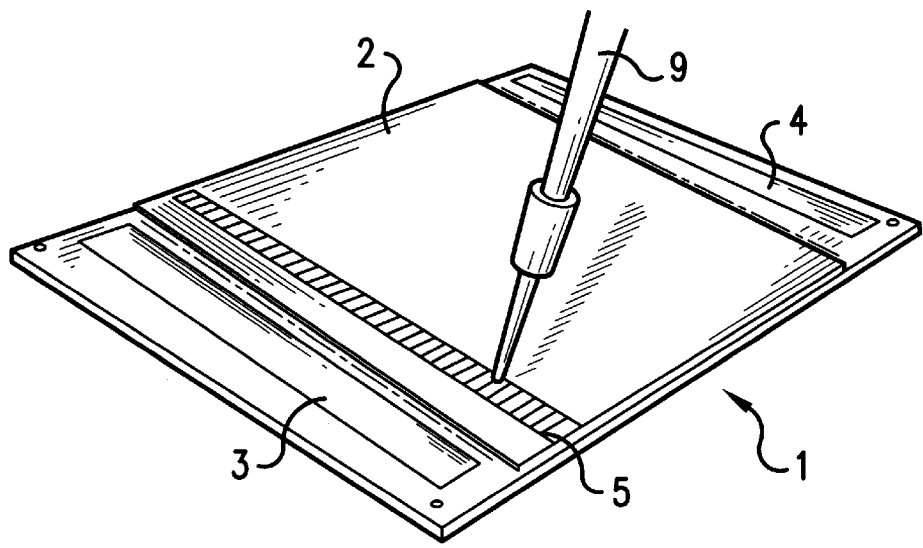
FIG. 2 is a second perspective view of the unit according to FIG. 1 in the process of depositing samples.

FIG. 2 shows a cassette unit 1 with the protective strips totally removed so that the buffer strips as well as a portion of the gel plate 2, which is provided with the sample wells, are exposed. 9 indicates a pipette for applying samples directly into the wells 5 in the exposed portion of the gel plate. The pipette 9 may be manually operated or automatically controlled with respect to the gel plate by means of a specific not shown device.

Figure 3:
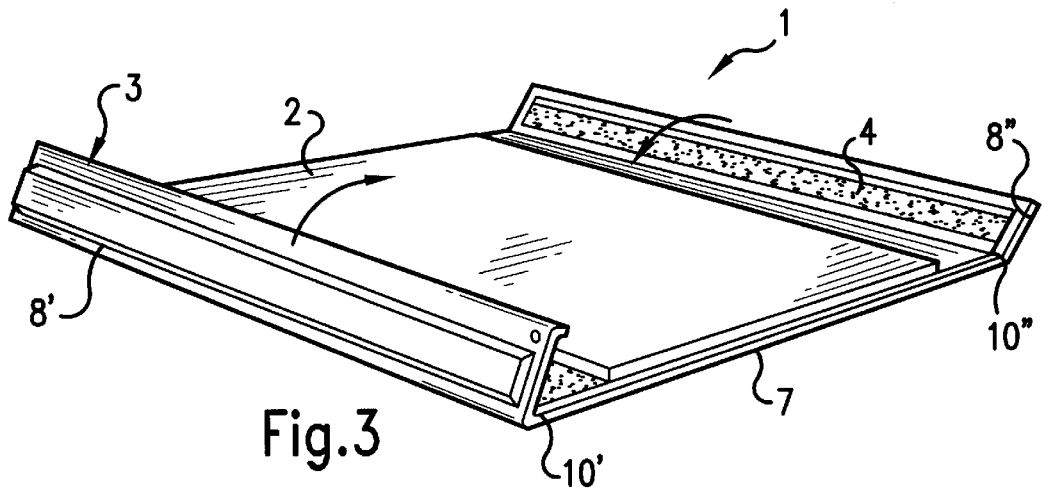
FIG. 3 is a perspective view of the unit according to FIG. 1 and 2 illustrating the process of displacing the buffer strips.

FIG. 3 shows the cassette unit where the buffer strips are brought from the inactive to the active position as indicated by the arrows. From this Figure it is clear that the wall means 7 and 8', 8" which are formed from a plastic material are connected by folding line portions 10', 10" allowing convenient and precise folding of the respective second wall means 8', 8" with respect to the first wall means 7.

Figure 4:
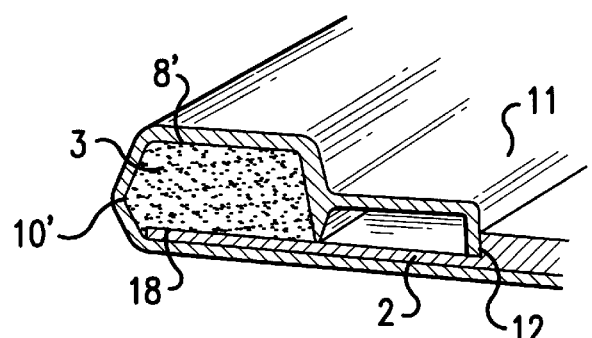
FIG. 4 is a partial sectional view illustrating the area around the buffer strip in the active position in an enlarged scale, FIGS. 5a and b illustrate an electrophoresis apparatus using a unit according to FIGS. 1–4.

The partial section according to FIG. 4 through the folded second wall means area shows this part in the active position, wherein the buffer strip on the second wall means 8' is applied firmly against the exposed portion of the gel plate so that the buffer strip and the gel plate are safely contacted at contact surface 18. At the edge of the second wall means which is distant from the folding line 10' there is provided a snap lock arrangement, wherein a strip of the second wall means at 12 snaps against a corresponding groove in the edge of the gel plate 2. The portion of the gel plate which is provided with the sample wells is protected by the cover strip 11 which may be provided with separate compartments for each sample load position so as to permit preparation of the cassette without any risk for mixing-up, contamination or transmission of infection.

The assembly is now ready or placing into an electrophoresis apparatus where it is to be subjected to the electric field so as to carry out the electrophoresis process.

Figure 5A:
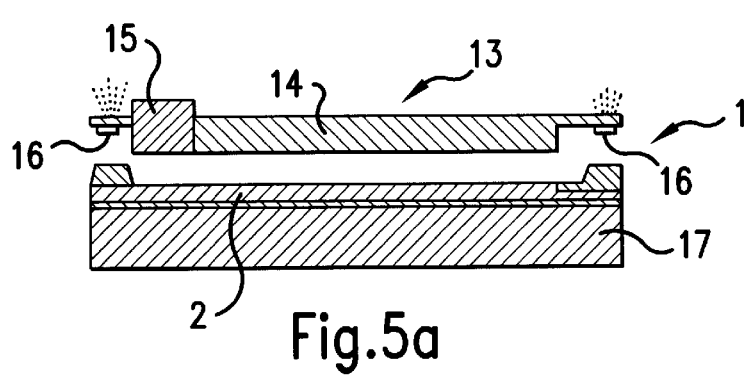

FIG. 5a diagrammatically shows an electrophoresis apparatus 13 which is intended to be used in connection with the gel cassette unit 1. To this end it includes a pressure pad 14 which carries also a laser and detection unit 15 for emitting layer radiation through the gel plate at a predetermined position in a per se known way. The pressure pad also carries electrodes 16 providing electrical contact between an outside source and the buffer strips. Further, the apparatus 13 includes a heater unit 17, which is also arranged to support the gel cassette unit in the electrophoresis process. When applying the pressure pad, which could be conveniently mounted on the lid of the instrument, the electrodes which are preferably spring loaded, contact the buffer strip so as to secure safe contact. The pad also assures even after contact of the unit 1 with the heater 17. The laser and detection unit is connected to per se known instruments for carrying out the analysis.

Figure 5B:
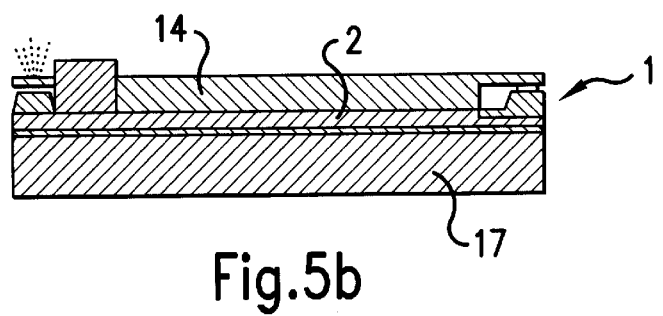
Figure 6A:
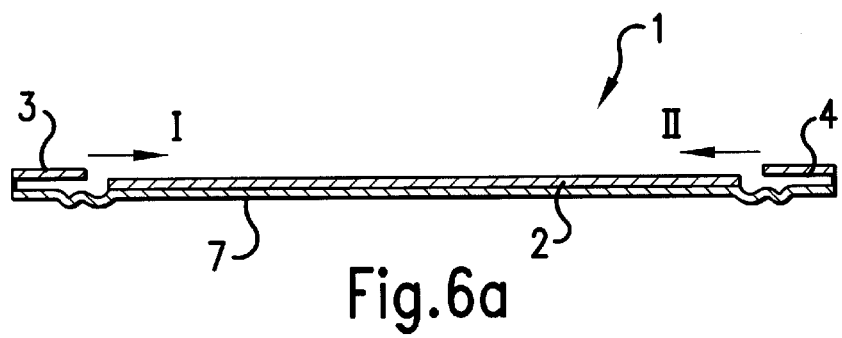
FIGS. 6a and b illustrate an alternative embodiment of a cassette unit according to the invention, and FIGS. 7a and b illustrate a second alternative embodiment of a cassette unit according to the invention.
Figure 6B:
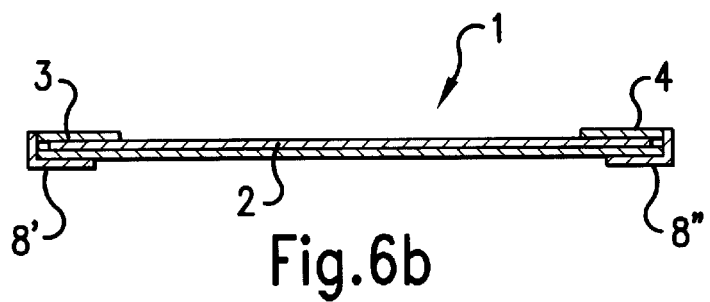

FIGS. 6a and 6b concern an alternative embodiment of the cassette unit 1, wherein buffer strips 3 and 4 are displaceable in a linear direction from an outside inactive position according to FIG. 6a where the parts are chemically and electrically separated from each other to an active position according to arrows I,II where the buffer strips 3 and 4, which are supported by the second wall means 8' and 8", respectively, are in the active position, see FIG. 6b. It may now be placed inside an electrophoresis instrument substantially according to FIGS. 5a and 5b.

It should be evident that the instrument as above is only mentioned as an example and that the cassette may be supported also e.g. vertically. The detection system and the pressure pad are also optional, since there are other means for carrying out the detection, such as by laser scanning or photography.

Figure 7A:
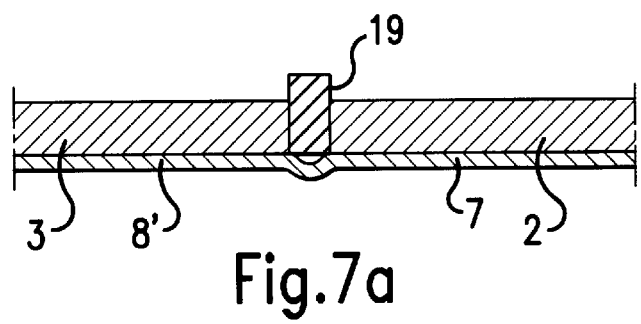
Figure 7B:
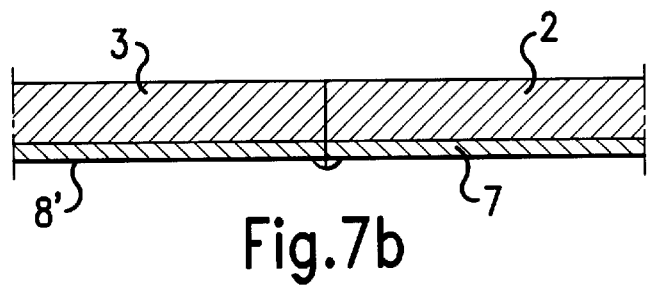

The invention is not limited to the above embodiments but only to the scope of the annexed claims. It is thus possible to obtain the displacement of the second wall means which carry the buffer strips otherwise than by pivoting and linear displacement. For example a combination of these two movements is possible. Another embodiment is illustrated in FIGS. 7a and 7b, wherein the gel plate 2 is separated from the buffer strip 3 by means of an isolator 19, which may be removed, whereafter the buffer strip 3 may be displaced sidewards so as to contact the gel plate 2 according to FIG. 7b. In an alternative embodiment, the isolator may be made from a substance which melts after heating whereby the required contact is established. It is also possible to arrange the buffer strips substantially as in FIG. 6b also in the inactive position, and in that case a removable isolating strip is placed between the surfaces to be contacted in the active position.

It should be noted that the first wall means for supporting the gel slab not necessarily has to be rigid of semi-rigid. In some cases it is satisfactory to have a flexible first wall means, which may be made from even a thin foil, for example of a plastic material. In that case the required support is provided by a support plate on the electrophoresis apparatus.

Instead of the sample wells of the embodiment shown, the gel slab may simply be provided with "sample load positions" which are not holes in the slab for the application of the samples. It is also possible in certain applications to use gel slabs where the samples are placed in any chosen position on the gel slab. One such case is where positively charged molecules migrate in the one direction and negatively charged molecules in the other direction. Loading may be accomplished also by placing a porous element which is soaked with sample liquid at the loading position. Further the invention is applicable also when placing buffer strips in other locations then opposite with respect to the gel slab, e.g. when carrying out two-dimensional electrophoresis.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A cassette for an electrophoresis system including an essentially plate shaped body, which comprises first wall means for supporting a gel plate and second wall means for supporting buffer strips, said wall means being connected to each other, wherein the second wall means are displaceable with respect to the first wall means between a first inactive position where the buffer strips are chemically and electrically separated from the gel plate and a second, active position where the buffer strips are in electrical and chemical contact with the gel plate.

2. The cassette according to claim 1, wherein the gel plate is provided with at least one sample load position.

3. The cassette according to claim 1, wherein the cassette is provided with a covering means providing separate cover for each sample load position.

4. The cassette according to claim 1, wherein the second wall means are displaceable by means of a linear movement.

5. The cassette according to claim 1, wherein the second wall means are displaceable by means of a pivoting movement.

6. The cassette according to claim 1, wherein the buffer strips are separated from the gel plate by means of removable isolating elements in the inactive position.

7. The cassette according to claim 1, wherein the buffer strips and at least a part of the gel plate are protected by protective strips in the inactive position.

8. An electrophoresis system including a support means, electrodes, an external electric power source and at least one cassette according to claim 1.

9. The electrophoresis system according to claim 8, further including a detection unit.

10. The electrophoresis system according to claim 9, further including a pressure pad for applying pressure to the cassette.

* * * * *